United States Patent [19]

Triedman et al.

[11] Patent Number: 5,848,972
[45] Date of Patent: Dec. 15, 1998

[54] METHOD FOR ENDOCARDIAL ACTIVATION MAPPING USING A MULTI-ELECTRODE CATHETER

[75] Inventors: John K. Triedman, Brookline; Kathy J. Jenkins, Cambridge; Steven D. Colan, Needham, all of Mass.

[73] Assignee: Children's Medical Center Corporation, Boston, Mass.

[21] Appl. No.: 713,429

[22] Filed: Sep. 13, 1996

Related U.S. Application Data

[60] Provisional application No. 60/006,901 Sep. 15, 1995.
[51] Int. Cl.$^6$ .................................................. A61B 5/0402
[52] U.S. Cl. ............................................................ 600/508
[58] Field of Search ................................... 434/262, 267, 434/272; 600/374, 378, 380, 382, 508, 523, 544, 546, 554

[56] References Cited

U.S. PATENT DOCUMENTS

| | | | |
|---|---|---|---|
| 3,516,400 | 6/1970 | Krohn et al. | 600/508 |
| 4,907,973 | 3/1990 | Hon | 434/272 |
| 5,022,412 | 6/1991 | Gracovetsky et al. | 600/382 |
| 5,137,548 | 8/1992 | Ungs et al. | 434/262 |
| 5,297,549 | 3/1994 | Beatty et al. | 600/374 |
| 5,331,960 | 7/1994 | Krenzke | 600/382 |
| 5,482,472 | 1/1996 | Garoni et al. | 434/272 |

OTHER PUBLICATIONS

Hauer, R.N.W. et al., "Endocardial Catheter Mapping: Validation of a Cineradiographic Method for Accurate Localization of Left Ventricular Sites" *Circulation*, vol. 74, pp. 862–868 (Oct. 1986).

Hauer, R.N.W. et al., "Endocardial Catheter Mapping: Wire Skeleton Technique for Representation of Computed Arrhythmogenic Sites Compared with Intraoperative Mapping" *Circulation*, vol. 7, pp. 1346–1354 (Dec. 1986).

Downar, E. et al., "Endocardial Mapping of Ventricular Tachycardia in the Intact Human Ventricle: Evidence for Reentrant Mechanisms" *JACC*, vol. 11, pp. 783–791 (Apr. 1988).

Mickleborough, L.L. et al., "Transatrial Balloon Technique for Activation Mapping During Operations for Recurrent Ventricular Tachycardia" *J. Thorac. Cardiovasc. Surg.*, vol. 99, pp. 227–233 (Feb. 1990).

Restivo, M. et al., "Ventricular Arrhythmias in the Subacute Mycocardial Infarction Period" *Circ. Res.*, vol. 66, pp. 1310–1327 (May 1990).

Masse, S. et al., "A Three–Dimensional Display for Cardiac Activation Mapping" *PACE*, vol. 14, pp. 538–545 (Apr. 1991).

(List continued on next page.)

*Primary Examiner*—William E. Kamm
*Attorney, Agent, or Firm*—Thomas J. Engellenner; Lawrence E. Monks; Lahive & Cockfield, LLP

[57] ABSTRACT

A system and method is disclosed to improve the ability of physicians, researchers and others to digest large amounts of cardiac electrophysiologic data acquired during cardiac catheterization, improving their ability to visualize, interpret and act on its content. The technique addresses previous limitations imposed by the number of electrodes which can be simultaneously recorded and by difficulty in determining their locations in reference to intracardiac anatomy. It is based on the composition of multiple activation sequence mappings made in a single rhythm, effected by referencing the position of each of the catheter electrodes to a measurement grid which is stable with respect to the patient's heart. Using this approach, the number of endocardial sites which can be sampled in a stable rhythm is theoretically unlimited, resulting in realization of high resolution activation maps. Rather than imposing a geometry determined primarily by the measurement apparatus, sites of measurement are scattered over the endocardial surface in a semi-random manner, and the real geometry of that surface may be reconstructed by measurements made of electrode position.

14 Claims, 3 Drawing Sheets

OTHER PUBLICATIONS

Schoels, W. et al., "Circus Movement Atrial Flutter in Canine Sterile Pericarditis Model" *Circulation*, vol. 83, pp. 1716–1730 (May 1991).

Calkins, H. et al., "Diagnosis and Cure of the Wolff–Parkinson–White Syndrome or Paroxysmal Supraventricular Tachycardias During a Single Electrophysiologic Test" *N. Engl. J. Med.*, vol. 324, pp. 1612–1618 (Jun. 1991).

Van Hare, G.F. et al., "Percutaneous Radiofrequency Catheter Ablation for Supraventricular Arrhythmias in Children" *JACC*, vol. 17, pp. 1613–1620 (Jun. 1991).

Lesh, M.D. et al., "Curative Percutaneous Catheter Ablation Using Radiofrequency Energy for Accessory Pathways in All Locations: Results in 100 Consecutive Patients" *JACC*, vol. 19, pp. 1303–1309 (May 1992).

Jackman, W.M. et al., "Treatment of Supraventricular Tachycardia Due to Atrioventricular Nodal Reentry by Radiofrequency Catheter Ablation of Slow–Pathway Conduction" *N. Engl. J. Med.*, vol. 327, pp. 313–318 (Jul. 1992).

Jenkins, K.J. et al., "Multipolar Endocardial Mapping of the Right Atrium During Cardiac Catheterization: Description of a New Technique" *J. Am. Coll. Cardiol.*, vol. 22, pp. 1105–1110 (Oct. 1993).

Yamauchi, S. et al., "Use of Intraoperative Mapping to Optimize Surgical Ablation of Atrial Flutter" *Ann Thorac Surg.*, vol. 56, pp. 337–342 (1993).

Kim, Y.H. et al., "Treatment of Ventricular Tachycardia by Transcatheter Radiofrequency Ablation in Patients with Ischemic Heart Disease" *Circulation*, vol. 89, pp. 1094–1102 (Mar. 1994).

Davis, L.M. et al., "Simultaneous 60–Electrode Mapping of Ventricular Tachycardia Using Percutaneous Catheters" *J. Am. Coll. Cardiol.*, vol. 24, pp. 709–719 (Sep. 1994).

Buckles, D.S. et al., "Image–Based Display of Activation Patterns Derived from Scattered Electrodes" *IEEE Trans. Biomed. Engin.*, vol. 42, pp. 111–115 (Jan. 1995).

Olgin, J.E. et al., "Role of Right Atrial Endocardial Structures as Barriers to Conduction During Human Type I Atrial Flutter" *Circulation*, vol. 92, pp. 1839–1848 (Oct. 1995).

Triedman, J.K. et al., "Radiofrequency Ablation of Intra–Atrial Reentrant Tachycardia After Surgical Palliation of Congenital Heart Disease" *Circulation*, vol. 91, pp. 707–714 (Feb. 1995).

Triedman, J.K. et al., "Right Atrial Mapping in Humans Using a Multielectrode Basket Catheter" *PACE*, vol. 18, p. 800 (Abstract) (Apr. 1995).

METHOD FOR ENDOCARDIAL ACTIVATION MAPPING USING A MULTI-ELECTRODE CATHETER

This invention was supported by funding from the National Institute for Health, under grant K08-HL03198. Consequently, The United States Government may have limited rights to the invention.

RELATED APPLICATIONS

The instant application is related to the copending provisional application, Ser. No. 60/006901, filed on Sep. 15, 1995, and abandoned as of Sep. 16, 1996 entitled "Rapid, High-Density Endocardial Activation Mapping by Composition of Multi-Electrode Catheter Recordings", and claims priority therefrom.

1. Field of the Invention

The current invention relates generally to methods for measuring electrical properties of anatomic organs, and more particularly to measuring and plotting the electrical properties of the endocardium using a multi-electrode catheter as probe and fluorography to identify position.

2. Background of the Invention

Catheter-based radio frequency (RF) ablative techniques have become the treatment of choice for curing many types of supraventricular tachycardia (SVT) in both children and adults. To perform a successful ablation, two issues must be addressed: the location of a vulnerable site must be identified by mapping the arrhythmia, and energy must be safely delivered to that site.

The arrhythmias which have been most amenable to RF ablation have been those types of SVT in which the appropriate Site for energy delivery is known and anatomically constant (e.g., AV node reentrant tachycardia), and those in which the accessory fiber mediating the SVT is known to traverse one of the two atrioventricular grooves. For these rhythms, the potentially complicated process of mapping electrical activation patterns in the heart can be reduced to identifying either an anatomic location, or a single point known to be located on the AV groove.

Unfortunately, a large group of patients, often with severe underlying cardiovascular disease, suffer from other, more intractable atrial or ventricular reentrant arrhythmias in which the vulnerable sites for ablation are not constrained in any simple manner by known cardiac anatomy. Although extensive experimental studies have demonstrated the reentrant pathways critical to such arrythmias, we are as yet unable to map these rhythms clinically in an easy, effective and reproducible manner. This is reflected in much the lower success rates for treatment of these rhythms using RF ablation.

As mentioned, there exists considerable experience in the construction of high density activation sequence maps of the atria and the ventricle in experimental applications, dating back almost 100 years. This generally involves surgical exposure of the endocardial and/or epicardial surface of the chamber to be mapped, and placement of an electrode grid of known geometry to record electrical activation. Although the nature of the techniques used to construct these maps is inherently complex and invasive, it has been possible to apply them intraoperatively to assist in the successful surgical resection of foci of ventricular tachycardia.

Structural constraints in catheter fabrication limit both the number of electrodes which can be simultaneously deployed in the heart and their geometry, and have precluded the development of similar useful techniques to assist RF ablation. Advances which have recently occurred in catheter design and signal processing technology have allowed a substantial increase in the number of electrical signals which can simultaneously be recorded in the catherization laboratory. Using the so-called "basket catheter" it is now feasible to record as many as 25 bipolar signals simultaneously from the atrium or ventricle. This number, however, is still far fewer than the optimal number for complete mapping of a cardiac chamber.

It is thus desirable to discover a method for complete mapping of a cardiactic chamber using a limited number of electrodes.

OBJECTS OF THE INVENTION

Due to the foregoing and other disadvantages of prior methods of measuring electrical activity and performing activation mapping of the endocardium or other anatomical structure, an object of this invention is to provide a method that allows one to make a large number of measurements during a stable rhythm of limited duration.

It is a further object of the invention to derive coordinates with respect to a defined coordinate system so as to describe the geometry of the endocardium or other anatomical structure.

It is a yet further object of the invention to derive coordinates with respect to a defined coordinate system so as to graphically map the geometry of the endocardium or other anatomical structure in three dimensions.

It is a still further object of the invention to animate on a graphical display electrical activation sequences associated with observed endocardial activity.

Other general and more specific objects of the invention will in part be obvious and will in part appear from the drawings and description which follow.

SUMMARY OF THE INVENTION

The present invention provides systems and methods for obtaining coordinate data representing the surface geometry of an anatomical structure. Furthermore, the methods and systems described herein disclose a system and method of obtaining data on electrical activity of the anatomic structure during a stable period which is suitable to be displayed using three dimensional graphical techniques.

This invention attains the foregoing and other objects with a novel method of which is summarized as follows.

For each electrical systole to be mapped, a multi-electrode catheter recording is made in an arbitrarily defined position in the heart of an arbitrary number of electrical channels appropriately amplified and filtered, and AP and lateral fluorogram frames are obtained to establish catheter position and orientation. Temporal and spatial reference points are established. A temporal reference point consists of a recurrent electrical event, used to reference activation times, which is associated with the rhythm of interest and easily identified on the surface ECG, for example, the onset of the P-wave in sinus rhythm. Spatial reference points, used to reference AP and lateral fluoroscopic locations of the basket electrodes, consist of any intrathoracic radiopaque objects occurring in the fluorographic field. Examples of these reference points might be surgical clips, sternal wires, or pacemaker leads.

For each recording, a four column numeric matrix is generated. The first three columns consist of spatial location in [X, Y, Z] Cartesian coordinates, taken from the AP and lateral fluoroscopic views of the catheter at the time the recording was made. The fourth column consists of activation times obtained during that recording, measured against the temporal reference point. These spatial and temporal measurements may be generated manually, from digital images using interactive, computer-assisted techniques, or completely automatically using image- and signal-processing software currently available.

An arbitrarily large number of such mappings can be made as long as the rhythm of interest is sustained and the fixed spatial and temporal reference points remain discernible. Between each recording, the catheter is moved by advancing or retracting it from the body, and/or rotating it, in order to sample another set of endocardial locations.

Because the spatial and temporal reference points are chosen to be as nearly identical as possible between individual recordings, the four column space-time array can be concatenated to form a much larger array which can be interpreted as a mapping of a single beat. However, due to cardiac movement, respiratory movement and inaccuracies in measurement, it is to be expected that a certain amount of error will be present in this data set, especially in the spatial measurement component. For this reason, it is desirable to employ algorithms to smooth the cloud of points generated in space, and/or time.

Display of activation sequence mapping can be effected by animating the three-dimensional spatial framework of the mapped cardiac chamber using activation time to represent the wave of electrical activity traversing the endocardial surface of the heart. After determining the total duration of the activation sequence to be animated, and specifying the isochronal window to be used for time steps, corresponding to individual frames of the animated sequence, and other details affecting the visual display. Using commercial software, the animated sequence may be replayed at any specified rate, thus allowing examination of the rhythm's activation sequence, and correlation of the anatomic pattern with the known fluoroscopic anatomy of the patient. Additionally, commercial software can be used to create the true illusion of depth using stereoptic projections with an appropriately chosen parallax angle. The three-dimensional data can be easily transformed into two-dimensional polar coordinates for graphing of activation times on paper. This is useful in the preparation of more standard forms of isochronal activation maps.

Other general and more specific objects of the invention will in part be obvious and will in part be evident from the drawings and description which follow.

BRIEF DESCRIPTION OF THE DRAWINGS

The foregoing and other objects, features and advantages of the invention will be apparent from the following description and apparent from the accompanying drawings, in which like reference characters refer to the same parts throughout the different views.

DESCRIPTION OF ILLUSTRATED EMBODIMENTS

The method and system described herein can be utilized advantageously to map the geometry of generic anatomic structures that allow for the placement of electrodes on the structure to sample electrical activity. This method is described in particular with regard to performing endocardial activation mapping using a multi-electrode catheter.

Figure 1:
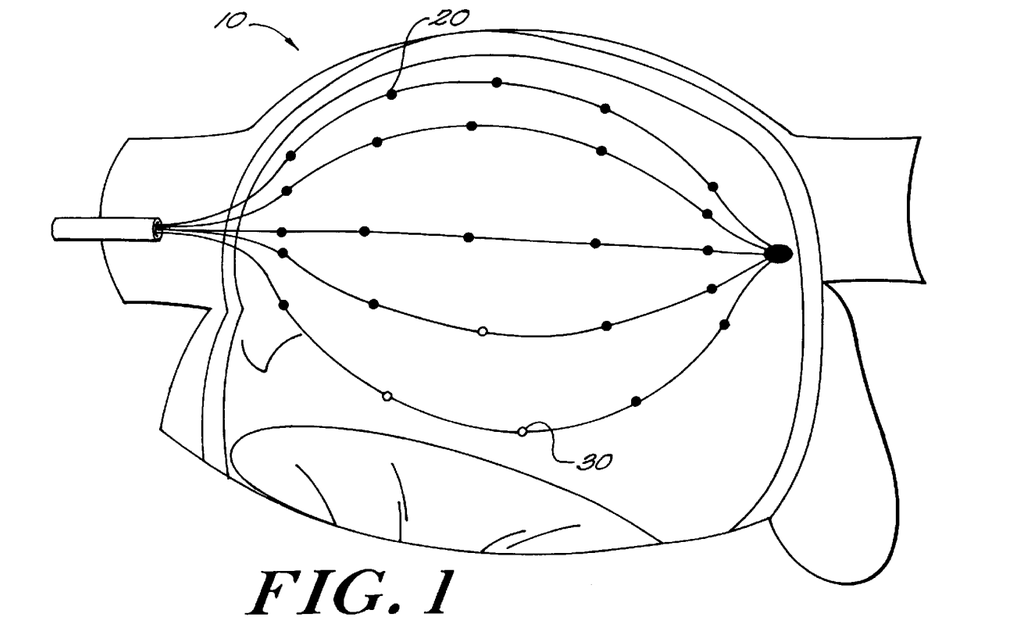
FIG. 1 is a depiction of a basket catheter with electrodes covering a portion of the surface of the endocardium.

Catheterization is performed under general anesthesia with femoral venous access. After estimation of the right atrial dimension is made by angiography, an appropriate Mullins sheath is used to guide a multi-electrode bipolar catheter 10 onto the right atrium so as to cover the organ, as shown in FIG. 1. In the preferred embodiment, a 50-electrode (25 bipolar pairs) catheter, the Webster-Jenkins Basket Catheter from Cordis-Webster, of Baldwin Park, Calif. is employed. One of ordinary skill in the art will recognize that a multi-electrode catheter of any geometry can be used to practice the invention. Endocardial contact is improved by expanding the basket with a coaxial puller mechanism attached to the catheter tip. In FIG. 1 filled circles 20 indicate electrode pairs registering atrial electrograms and open circles 30 indicate electrode pairs with no discernible electron activity due to absence of close proximity to the endocardial wall.

Figure 2:
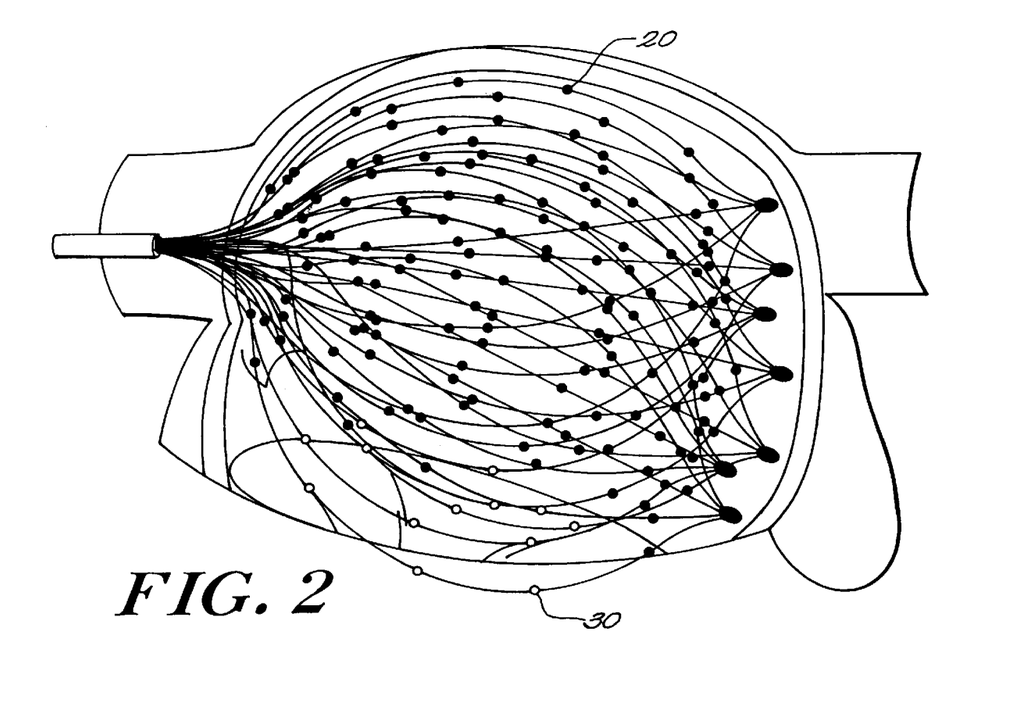
FIG. 2 is a depiction of a plurality of superimposed electrode locations after the basket catheter has be moved multiple times.

Multiple recordings of atrial activation times are obtained of a stable rhythm consisting of a plurality of periods, with the basket rotated, advanced and retracted in the atrium to sample as much of the endocardial surface as possible. FIG. 2 depicts the universe of sampled points of the endocardium after the completion of the sampling. Atrial activation times were determined for each electrode pair bearing a signal using electronic calipers after selection of a constant fiducial point. Examples of this temporal reference might be onset of P-wave, pacing artifact, or esophageal clectrogram. Total right atrial activation times are calculated as the duration in milliseconds from the earliest to the latest atrial electrograms recorded from all electrode pairs during a given atrial rhythm. Rotation and repositioning of the multi-electrode catheters allow acquisition of a high density mapping of endocardial points.

For studies in which several discrete recordings of a stable rhythm of interest are available, approximation of the mapped endocardial surface in 3 dimensions is achieved by identifying the spatial locations of recording electrode pairs with biplane fluorography, using a modified model of the technique previously described by Hauer et al., Hauer R N W, Heethaar R M, dezwart M T, van Dijk R N, van der Tweel I, Borst C, Robles de Medina E O: Endocardial catheter mapping: validation of a radiographic method for accurate localization of left ventricular sites. *Circulation* 1986;74:862 which is incorporated by reference herein. Coordinates of individual electrode pairs and fixed intrathoracic reference points (e.g., surgical clips and wires) are obtained in orthogonal views and used to generate an [X Y Z]-Cartesian coordinate vector for each measured point, using both manual and computer-assisted (Adobe Photoshop v3.1, Optimas v5.1a) techniques. More particularly, each recording is documented with fluorograms, utilizing conventional fluoroscopy. The fluorograms are taken in AP and lateral views to establish catheter electrode locations. These fluorograms are used to establish the two planes defining for example the XY, and YZ planes for spatial locationing. The third plane, XZ, is derived from the other two by taking the appropriate coordinates from the other two planes. The planes define the rectangular Cartesian coordinates of the electrode locations and thus describe the geometry of the anatomical structure. Two reference markers such as staples, clips or the like are positioned so as to define absolute spatial reference points for the anatomic structure, in this case the endocardium. Most conveniently, one of the markers is initially designated as the origin of the coordinate system, and the other marker is used to define the coordinate system relative to that origin. Using the two fluorograms and the markers establishing reference points, the geometry of the structure is mapped by measuring distances of the structure to be mapped from the two fluoroscopic views, relative to the established coordinate system. In the preferred embodiment the two fluorograms are orthogonal views of the organ, in order to reduce the mathematical complexity of the derivations. However, one of ordinary skill in the art will recognize that the planes are not required to be orthogonal, only that they be non coplanar with a known angle of rotation about their common axis. In cases where electrode location is not well-delineated, symmetry of catheter design is used to interpolate electrode pair location when possible. Alignment of spatial locations of pairs from multiple recordings was achieved by subtraction of the [X Y Z]-coordinates of the reference markers.

Scaling to accommodate differences in magnification between the orthogonal view was accomplished using the slope of the linear regression equation relating the points identified along the craniocaudal axis of each view.

Figure 4:
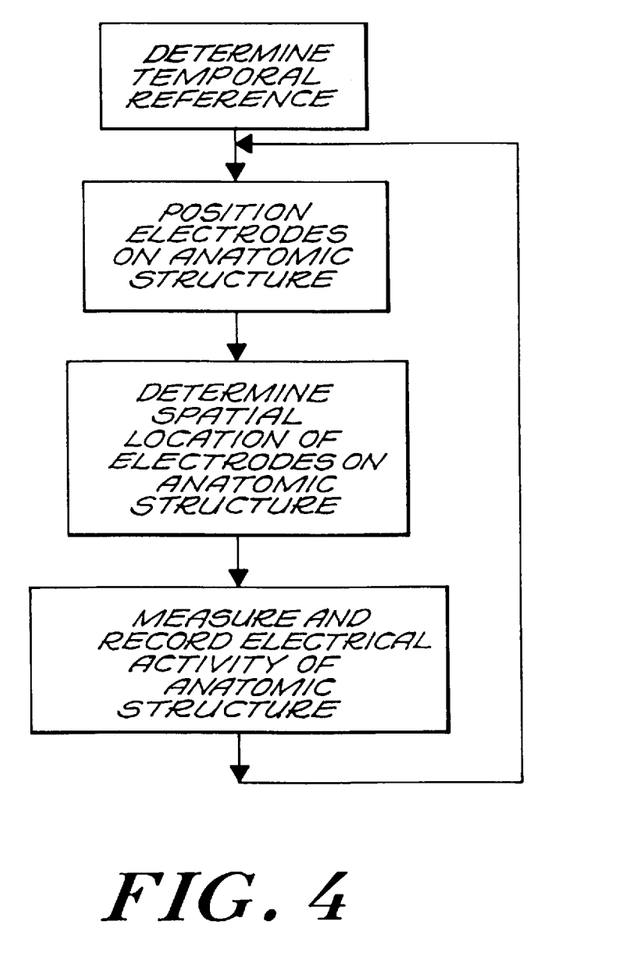
FIG. 4 is a flow chart of the method of the instant invention.

FIG. 4 depicts a flow chart of the procedure.

Figure 3:
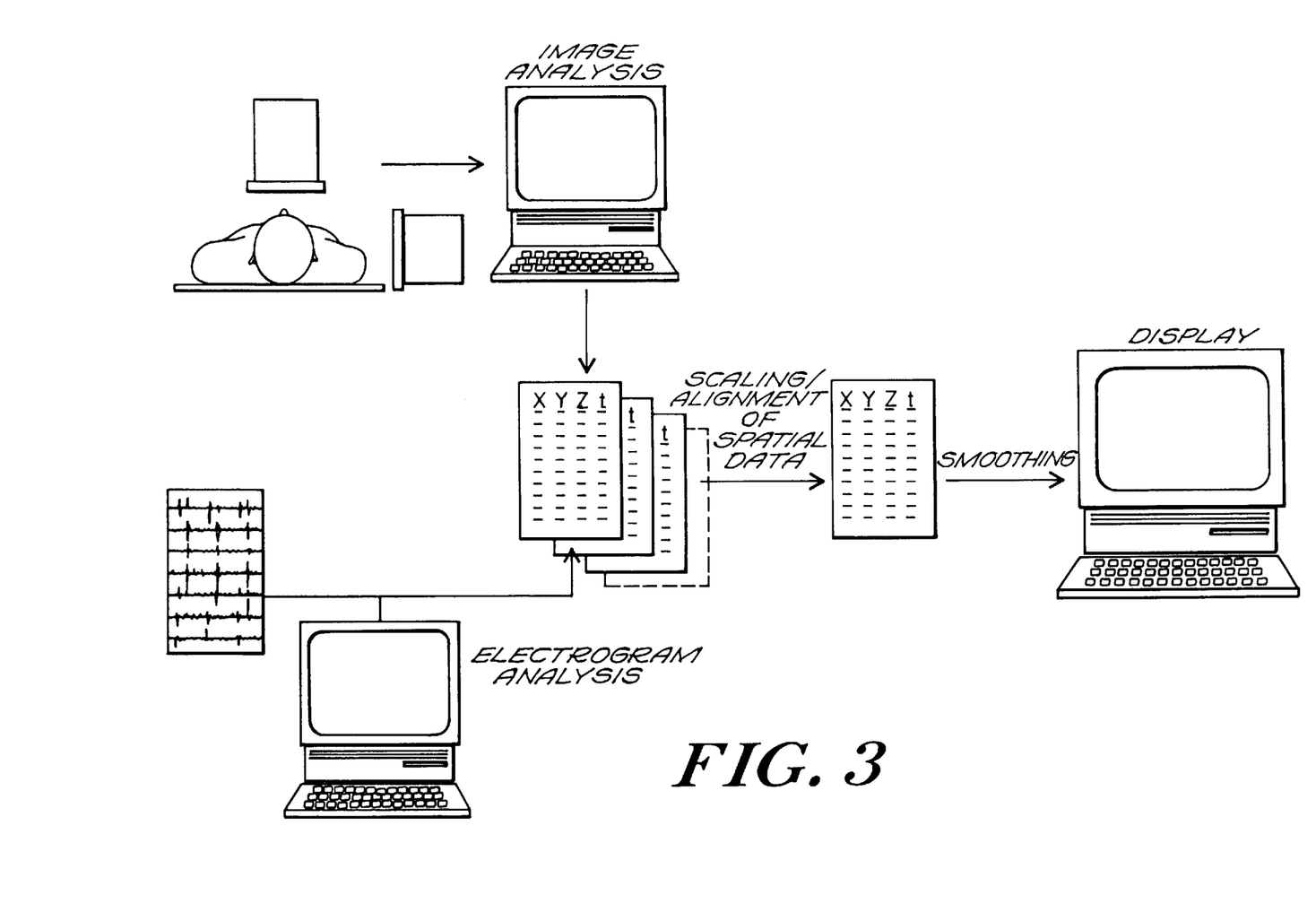
FIG. 3 is a diagram setting forth the system processing of electrophysiologic and fluoroscopic signals to obtain animated activation sequences.

Processing of raw fluorographic and electrophysiologic data for display is outlined in FIG. 3. Employing the assumption that spatial and temporal reference points are "constant" (based on selection criteria) between recordings, data from individual records was combined to increase mapping density. To reduce the error in spatial measurement due to cardiorespiratory motion and other causes, spatial locations are smoothed using an algorithm developed for this purpose, based on a spherical approximation of true endocardial geometry. The matrix of spatial [X Y Z] data representing the mapped endocardial points for a single beat is converted to a zero-mean matrix by subtracting the mean spatial position of all points:

$$[X\ Y\ Z\ ]_0 = [X\ Y\ Z\ ] - [x\ y\ z\ ]mean \quad 1)$$

Data points are then converted to spherical coordinates [ρθφ]:

$$\rho = (x^2+y^2+z^2)^{1/2} \quad 2)$$

$$0\theta = \cos^{-1}[x/(x^2+y^2)^{1/2}], y \geq 0 \quad 3)$$

$$0\theta = 2\rho - \cos^{-1}[x/(x^2+y^2)^{1/2}],\ y<0 \quad 4)$$

$$\phi = \rho/2 - \cos^{-1}[(x^2+y^2)^{1/2}/\rho], z \geq 0 \quad 5)$$

$$\phi = \rho/2 + \cos^{-1}[(x^2+y^2)^{1/2}/\rho], z<0. \quad 6)$$

Smoothing was then performed by averaging the values of ρ, representing the vector length of a point from the approximate center of the atrium, with the ρ-values of its near neighbors determined using the angular coordinates θ and φ. The size of the "neighborhood" and thus the degree of smoothing is determined by the user as a fraction of the surface area (FSA) of the unit sphere, which is converted into an arc length using the formula:

$$\text{arc length} = \cos^{-1}(1-2\times FSA). \quad 7)$$

Thus, specifying an FSA of 0 results in no smoothing, while a FSA of 1.0 results in all values of ρ being averaged over the entire sphere. In the preferred embodiment, low FSA values of 0.03–0.05 are chosen empirically, to preserve as much anatomic detail as possible in the maps.

In summary in order to reduce the artifactual effect of mechanical motion on the reconstructed image of the atrial endocardial surface, the following algorithm for spherical smoothing is implemented:

1. A zero-mean spatial array is created by subtracting the mean [X Y Z]-coordinate for the entire array from each point of the data array [X Y Z];
2. The zero-mean array is converted from [X Y Z]-coordinates to a spherical coordinate system ([ρθφ]-coordinates);
3. A user-specified smoothing factor indicating the fractional surface area of a sphere over which smoothing should occur (0.04–0.08) is converted into a reference arc measured in steradians;
4. For each point, ρ is reset to its mean value for all rays intersecting the arc specified by the smoothing factor and centered on the ray defined by θ and φ;
5. The smoothed [ρθφ]-coordinate array is reconverted to [X Y Z]-coordinates to facilitate display.

This algorithm smoothes the spatial data using a spherical template. A smoothing factor of 1.0 results in all points being mapped to a perfect sphere with a radius equal to the mean radius of all points, while a smoothing factor of 0 results in no smoothing.

Having derived the set of points that define the surface geometry of the anatomical structure, in this case the endocardium, commercially available software may be advantageously utilized to draw a three dimensional view of the structure. MATLAB from MathSoft of Natick, Mass. is one such software package that will allow one to display a three dimensional image, defined by coordinates. Associated with each coordinate point is a time of electrical activation. Thus, again using commercially available software such as MATLAB maps of electrical activation in the structure can be derived and displayed. Producing maps of activation sequences, over time, allows one to display an animation of electrical activity in the anatomical structure.

Activation sequence maps are animated by superimposing activation times on the three-dimensional spatial framework, to represent the wave of electrical activity traversing the endocardial surface of the heart. Displays are projected in 3-dimensions from a point of view which can be specified by the user. Isochronal windows for time increments corresponding to individual frames of the animated sequence are also user-specified. The presentation software is also used to create the illusion of depth by using appropriate stereoptic projections. This technique further enhances the ability of the viewer to appreciate the third dimensional component of the activation sequence.

It will thus be seen that the invention efficiently attains the objects set forth above, among those made apparent from the preceding description. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and desired to be secured by Letters Patent is:

1. A method for spatially mapping the electrical activity of an anatomic structure, said method comprising of the steps of:

(a) determining a temporal reference;
   (b) positioning at least one electrode pair on the surface of said anatomic structure;
   (c) determining by means of a fluoroscope the spatial location of each positioned electrode pair;
   (d) measuring electrical activity at each electrode pair;
   (e) recording for each electrode pair said measurement of electrical activity, the time of measurement of electrical activity for each electrode pair relative to said temporal reference, and the spatial location of each electrode pair;
   (f) repetitively performing steps (b) through (e) to map the electrical activity of the anatomic structure.

2. The method of claim 1 wherein the said anatomical structure to be mapped is the endocardium.

3. The method of claim 1 wherein the step of determining a temporal reference further includes identifying a periodic time signal and measuring electrical activity at a fixed interval from said periodic time signal.

4. The method of claim 3 wherein identifying a periodic time signal further includes identifying an onset of a P-wave in sinus rhythm for a heart.

5. The method of claim 3 wherein identifying a periodic time signal includes identifying a pacing artifact.

6. The method of claim 3 wherein the step of determining a temporal reference includes performing an esophageal electrogram.

7. The method of claim 1 wherein the step of determining by means of a fluoroscope the spatial location of each positioned electrode pair includes relating the location of each said electrode pair to a coordinate system.

8. The method of claim 7 wherein relating the location of each said electrode pair to a coordinate system includes positioning a first reference marker on said anatomical structure for identifying the origin of said coordinate system.

9. The method of claim 8 wherein positioning a first reference marker includes selecting said reference marker from the group of clips and staples.

10. The method of claim 8 wherein the step of determining by means of a fluoroscope the spatial location of each said electrode pair includes positioning a second reference marker on said anatomical structure and determining distance in said coordinate system by reference to said first and second reference markers.

11. The method of claim 1 wherein the step of determining by means of a fluoroscope the spatial location of each positioned electrode pair includes relating the location of each said electrode pair to a Cartesian coordinate system.

12. The method of claim 1 wherein the step of determining by means of a fluoroscope the spatial location of each positioned electrode pair includes relating the location of each said electrode pair to a spherical coordinate system.

13. The method of claim 1 wherein the step of determining by means of a fluoroscope the spatial location of each positioned electrode pair includes relating the location of each said electrode pair to a spherical coordinate system.

14. The method of claim 1 wherein the step of determining by means of a fluoroscope the spatial location of each positioned electrode pair includes relating the location of each said electrode pair to a Cartesian coordinate system.

* * * * *

UNITED STATES PATENT AND TRADEMARK OFFICE
CERTIFICATE OF CORRECTION

| | |
|---|---|
| PATENT NO. : | 5,848,972 |
| DATED : | December 15, 1998 |
| INVENTOR(S) : | John K. Triedman et al. |

It is certified that error appears in the above-indentified patent and that said Letters Patent is hereby corrected as shown below:

1) Col. 5, line 49 (equation 3):  Reads:  $0\theta = \cos^{-1}[x/(x^2 + y^2)^{1/2}], y \geq \theta 0$ Should read:  $\theta = \cos^{-1}[x/(x^2 + y^2)^{1/2}], y \geq 0$ 2) Col. 5, line 51 (equation 4):  Reads:  $0\theta = 2\rho - \cos^{-1}[x/(x^2 + y^2)^{1/2}], y < \theta 0$ Should read:  $\theta = 2\rho - \cos^{-1}[x/(x^2 + y^2)^{1/2}], y < 0$ 3) Col. 5, line 53 (equation 5):  Reads:  $\phi = \rho/2 - \cos^{-1}[(x^2 + y^2)^{1/2}/\rho], z \geq \theta 0$ Should read:  $\phi = \rho/2 - \cos^{-1}[(x^2 + y^2)^{1/2}/\rho], z \geq 0$

UNITED STATES PATENT AND TRADEMARK OFFICE
CERTIFICATE OF CORRECTION

PATENT NO. : 5,848,972
DATED : December 15, 1998
INVENTOR(S) : John K. Triedman, et. al.

It is certified that error appears in the above-identified patent and that said Letters Patent is hereby corrected as shown below:

4) Col. 5, line 55 (equation 6):   Reads: $\phi = \rho/2 - \cos^{-1}[(x^2 + y^2)^{1/2}/\rho], z < \theta 0$ Should read: $\phi = \rho/2 - \cos^{-1}[(x^2 + y^2)^{1/2}/\rho], z < 0$ Signed and Sealed this Fourth Day of April, 2000

Q. TODD DICKINSON

Attest:

Attesting Officer

Director of Patents and Trademarks